United States Patent
Olson

(10) Patent No.: US 12,171,489 B2
(45) Date of Patent: Dec. 24, 2024

(54) ELECTROPORATION SYSTEM AND METHOD OF ENERGIZING A CATHETER

(71) Applicant: St. Jude Medical, Cardiology Division, Inc., St. Paul, MN (US)

(72) Inventor: Eric Olson, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/242,738

(22) Filed: Sep. 6, 2023

(65) Prior Publication Data

US 2023/0404657 A1 Dec. 21, 2023

Related U.S. Application Data

(63) Continuation of application No. 17/964,338, filed on Oct. 12, 2022, now Pat. No. 11,786,301, which is a
(Continued)

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00214* (2013.01);
(Continued)

(58) Field of Classification Search
None
See application file for complete search history.

(56) References Cited

U.S. PATENT DOCUMENTS 11,497,550 B2 * 11/2022 Olson ............... A61N 1/327
11,786,301 B2 * 10/2023 Olson ............... A61B 18/1206
606/41
(Continued)

FOREIGN PATENT DOCUMENTS

JP 2016515442 A 5/2016
WO 2013052590 A1 4/2013
(Continued)

OTHER PUBLICATIONS

International Search Report and Written Opinion for International Application No. PCT/US2018/026679, dated Jun. 27, 2018, 13 pages.

*Primary Examiner* — Michael F Peffley
*Assistant Examiner* — Nicholas S Borsch
(74) *Attorney, Agent, or Firm* — Armstrong Teasdale LLP

(57) ABSTRACT

The present disclosure provides electroporation systems and methods of energizing a catheter for delivering electroporation. A catheter for delivering electroporation includes a distal section and an electrode assembly. The distal section is configured to be positioned in a vein within a body. The vein defines a central axis. The electrode assembly is coupled to the distal section and includes a structure and a plurality of electrodes distributed thereabout. The structure is configured to at least partially contact the vein. Each of the electrodes is configured to be selectively energized to form a circumferential ring of energized electrodes that is concentric with the central axis of the vein.

15 Claims, 7 Drawing Sheets

Related U.S. Application Data continuation of application No. 16/493,336, filed as application No. PCT/US2018/026679 on Apr. 9, 2018, now Pat. No. 11,497,550.

(60) Provisional application No. 62/483,749, filed on Apr. 10, 2017.

(52) U.S. Cl.
CPC ............... *A61B 2018/00345* (2013.01); *A61B 2018/00613* (2013.01); *A61B 2018/00654* (2013.01); *A61B 2018/1266* (2013.01); *A61B 2018/1467* (2013.01)

(56) References Cited

U.S. PATENT DOCUMENTS

| | | | |
|---|---|---|---|
| 2002/0177765 | A1 | 11/2002 | Bowe et al. |
| 2010/0073150 | A1 | 3/2010 | Olson et al. |
| 2010/0204560 | A1 | 8/2010 | Salahieh et al. |
| 2011/0137284 | A1 | 6/2011 | Arora et al. |
| 2012/0059255 | A1* | 3/2012 | Paul ................ A61B 18/14 600/431 |
| 2012/0071870 | A1 | 3/2012 | Salahieh et al. |
| 2014/0357956 | A1* | 12/2014 | Salahieh ............. A61B 5/6858 348/77 |
| 2016/0256682 | A1 | 9/2016 | Paul et al. |
| 2017/0065339 | A1* | 3/2017 | Mickelsen ............. A61N 1/327 |
| 2018/0042674 | A1 | 2/2018 | Mickelsen |
| 2018/0064494 | A1 | 3/2018 | Hareland |

FOREIGN PATENT DOCUMENTS

| | | | |
|---|---|---|---|
| WO | 2015171921 | A2 | 11/2015 |
| WO | 2015175944 | A1 | 11/2015 |

* cited by examiner

ELECTROPORATION SYSTEM AND METHOD OF ENERGIZING A CATHETER

CROSS REFERENCE OF RELATED APPLICATION

This application is a continuation of U.S. Non-Provisional application Ser. No. 17/964,338, filed on Oct. 12, 2022, which is a continuation of U.S. Non-Provisional application Ser. No. 16/493,336, filed on Sep. 12, 2019, which is the national stage entry of PCT/US2018/026679, filed on Apr. 9, 2018, which claims the benefit of priority to U.S. Provisional Application Ser. No. 62/483,749, filed Apr. 10, 2017, all of which are incorporated by reference herein in their entirety.

FIELD OF THE DISCLOSURE

The present disclosure relates generally to medical devices that are used in the human body. In particular, in many embodiments, the present disclosure relates to electroporation systems and methods of energizing a catheter for delivering electroporation.

BACKGROUND

It is generally known that ablation therapy may be used to treat various conditions afflicting the human anatomy. One such condition in which ablation therapy finds a particular application in, for example, is the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow that can lead to a variety of ailments and even death. It is believed that the primary cause of atrial arrhythmia is stray electrical signals within the left or right atrium of the heart. The ablation catheter imparts ablative energy (e.g., radio frequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric field induced pore formation on the cell membrane. The electric field may be induced by applying a direct current (DC) signal delivered as a relatively short duration pulse that may last, for instance, from a nanosecond to several milliseconds. Such a pulse may be repeated to form a pulse train. When such an electric field is applied to tissue in an in vivo setting, the cells in the tissue are subjected to trans-membrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

BRIEF SUMMARY OF THE DISCLOSURE

The present disclosure generally relates to electroporation systems and methods of energizing a catheter for delivering electroporation. In many embodiments, the electroporation system includes a catheter connected to a direct current (DC) energy source. The catheter and DC energy source are further connected to a computing system that, in certain embodiments, enables three-dimensional or two-dimensional visualization of the catheter within a vein of a body. The catheter includes an electrode assembly having a structure about which a plurality of electrodes is distributed. The structure may include, for example, a hoop catheter, a basket catheter, or a balloon catheter. The electrodes may include, for example, flexible circuits, printed electrodes, or ring electrodes. In many embodiments, the computing system determines positioning of the catheter in the vein and controls the DC energy source to energize selected electrodes of the plurality. The selection of the electrodes, in certain embodiments, is automatic. In other embodiments, the selection of electrodes is made by a clinician or physician based on a visualization. The selected electrodes to be energized form a ring of electrodes that is concentric with a central axis of the vein in which the catheter is positioned. Other embodiments and descriptions of the present disclosure are set forth below.

In one embodiment, the present disclosure provides a catheter for delivering electroporation. The catheter includes a distal section and an electrode assembly. The distal section is configured to be positioned in a vein within a body. The vein defines a central axis. The electrode assembly is coupled to the distal section and includes a structure and a plurality of electrodes distributed thereabout. The structure is configured to at least partially contact the vein. Each of the electrodes is configured to be selectively energized to form a circumferential ring of energized electrodes that is concentric with the central axis of the vein.

In another embodiment, the present disclosure is directed to an electroporation system, including a catheter, a DC energy source, and a computing system. The catheter includes an electrode assembly configured to be positioned in a vein of a body. The vein defines a central axis. The electrode assembly includes a structure configured to at least partially contact the vein, and a plurality of electrodes distributed about the structure. Each electrode of the plurality of electrodes is configured to be individually energized. The DC energy source is coupled to the catheter and is configured to selectively energize a subset of electrodes of the plurality of electrodes. The computing system is coupled to the catheter and the DC energy source. The computing system configured to detect respective positions of the plurality of electrodes within the vein, and select the subset of electrodes to form a circumferential ring of energized electrodes that is concentric with the central axis of the vein.

In another embodiment, the present disclosure is directed to a method of energizing a catheter. The method includes positioning a distal section of the catheter relative to a central axis in space. The distal section includes a plurality of electrodes distributed about a structure, and the structure at least partially surrounds the central axis. The method includes determining respective locations of the plurality of electrodes relative to the central axis. The method includes selecting a subset of electrodes from among the plurality of electrodes based on the respective locations thereof to form a circumferential ring of electrodes that is concentric with the central axis. The method includes energizing the subset of electrodes.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to electroporation systems and methods of energizing a catheter for delivering irreversible electroporation (IRE) using intracardiac catheters, such as, for example, a spiral catheter, or "voltage" catheter, that delivers a high-voltage to multiple electrodes through which a therapeutic current flows into a pulmonary vein of the left atrium of the heart. During such a procedure, a physician maneuvers the catheter to place it the ostia or antrum of a pulmonary vein. The catheter should be oriented, preferably, such that a hoop of the catheter is concentric with the central axis of the pulmonary vein. It is realized herein that achieving such an orientation is challenging, potentially requiring multiple attempts and, in certain circumstances, a proper position and orientation of the catheter cannot be achieved. It is further realized herein that it is desirable to simplify the task of placing the catheter for better concentricity and to reduce the time to place the catheter. It is also desirable to ensure the electrodes of the catheter contact the cardiac tissue. Contact can be difficult to achieve due to the variable shape and eccentricity of pulmonary veins, the complexity of the endocardium and entrance to the pulmonary veins, and due to the catheter's circular shape and limited ability to deform.

Embodiments of the electroporation systems described herein provide a catheter having a constellation of electrodes that, when placed in the pulmonary vein and mapped, are selectively energized to form a ring of electrodes concentric with the central axis of the pulmonary vein and through which a therapeutic IRE current is delivered. The catheter is mapped by a navigation system that, in certain embodiments, provides a visualization and interface for the physician. In certain embodiments, the catheter is a basket catheter that can be placed in a collapsed state such that it can be maneuvered as a linear catheter. Such a catheter is then expanded within the pulmonary vein to ensure contact around a full circumference of the pulmonary vein. The selected ring of electrodes establishes a virtual ring or virtual spiral of electrodes that is as operably effective at delivering IRE current as an ideally placed hoop or spiral catheter, but with substantially greater ease in placement. It is contemplated, however, that the described features and methods of the present disclosure as described herein may be incorporated into any number of systems as would be appreciated by one of ordinary skill in the art based on the disclosure herein.

Figure 1:
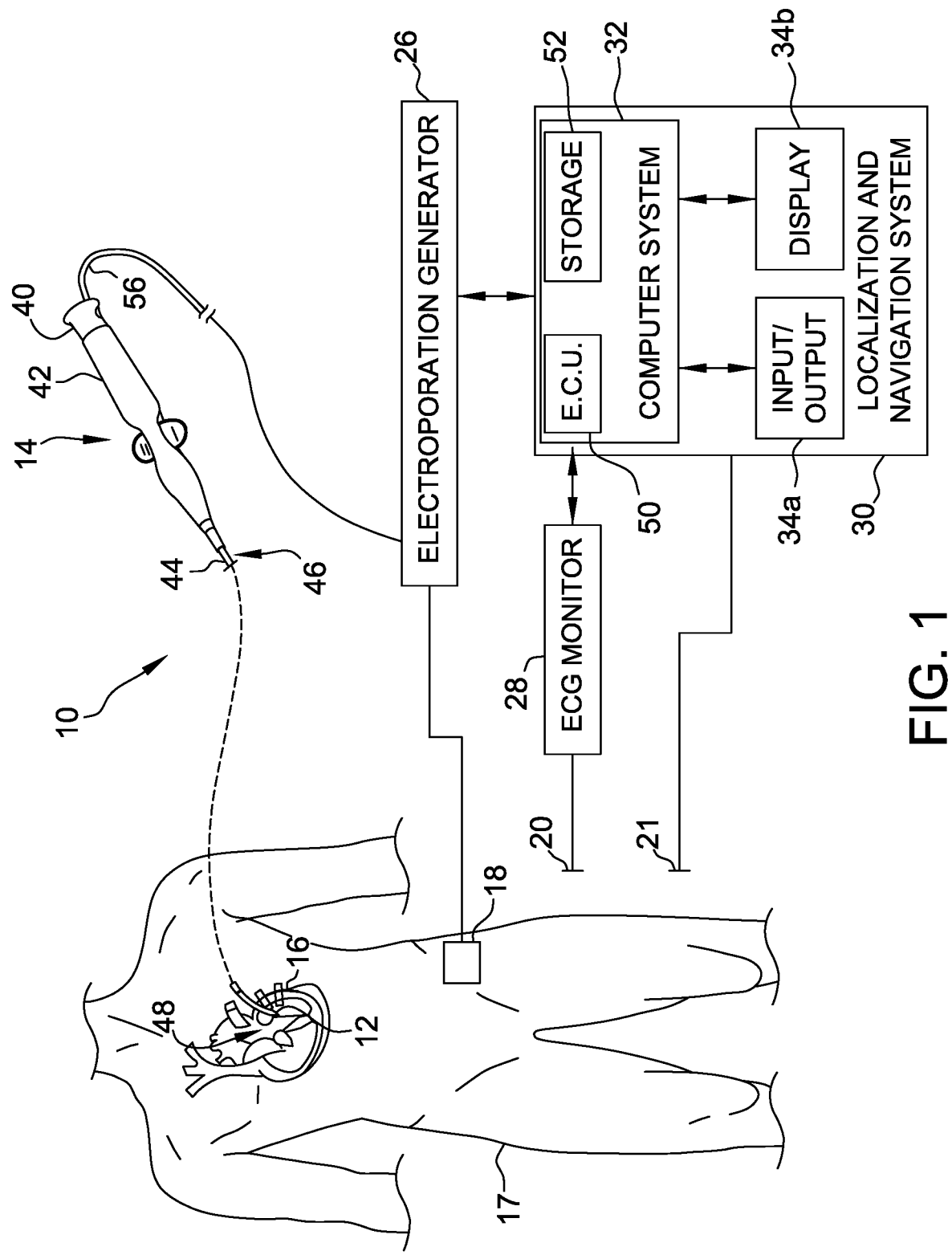
FIG. 1 is a schematic and block diagram view of a system incorporating embodiments for electroporation therapy.

Referring now to the drawings, FIG. 1 is a diagrammatic and block diagram view of a system 10 for electroporation therapy. In general, the various embodiments include an electrode assembly disposed at the distal section of a catheter. As used herein, "proximal" refers to a direction toward the end of the catheter near the clinician and "distal" refers to a direction away from the clinician and (generally) inside the body of a patient. The "distal section" of the catheter refers generally to the section of the catheter, at or near the distal end, that is inserted into the body of the patient. Moreover, embodiments described herein are not limited to those having electrode assemblies disposed at the distal end of the catheter, and instead include embodiments where the catheter, in the distal region, extends beyond the electrode assembly in the distal direction by some length. The electrode assembly includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering an electric field strength of about 0.1 to 1.0 kV/cm.

Irreversible electroporation through a multi-electrode hoop catheter may enable pulmonary vein isolation in as few as one shock per vein, which may produce much shorter procedure times compared to sequentially positioning a radiofrequency (RF) ablation tip around a vein.

It should be understood that while the energization strategies are described as involving DC pulses, embodiments may use variations and remain within the spirit and scope of the invention. For example, exponentially-decaying pulses, exponentially-increasing pulses, and combinations may be used.

It should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

With this background, and now referring again to FIG. 1, system 10 includes a catheter electrode assembly 12 including a constellation, or array, of catheter electrodes configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various sub-systems included in the overall system 10, such as an electroporation generator 26, an electrophysiology (EP) monitor such as an ECG monitor 28, and a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, the constellation of catheter electrodes. Return electrodes that are catheter electrodes may be part of electrode assembly 12 or part of a separate catheter (not shown). System 10 may further include a computer system 32 (including an electronic control unit 50 and data storage—memory 52) integrated with localization and navigation system 30 in certain embodiments. Computer system 32 may further include conventional interface components, such as various user input/output mechanisms 34a and a display 34b, among other components.

Electroporation generator 26 is configured to energize the electrode element(s) in accordance with an electroporation energization strategy that may be predetermined or may be user-selectable. The electrode elements may include unipole electrodes, bipole electrodes, or a combination of both. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude is increased to achieve electroporation.

Electroporation generator 26, sometimes referred to herein as a DC energy source, is a monophasic electroporation generator 26 configured to generate a series of DC energy pulses that all produce current in the same direction. In other embodiments, electroporation generator is biphasic or polyphasic electroporation generator configured to produce DC energy pulses that do not all produce current in the same direction. For successful electroporation, some embodiments utilize a two hundred joule output level. Electroporation generator 26 may output a DC pulse having a peak magnitude of between about negative one kilovolt (kV) and about negative two kV at the two hundred joule output level. In some embodiments, electroporation generator 26 outputs a DC pulse having a peak magnitude between about negative 1.5 kV and about negative 2.0 kV. Other embodiments may output any other suitable voltage, including a positive voltage. In some embodiments, electroporation generator 26 is a monophasic defibrillator such as, for example, a Lifepak 9 defibrillator available from Physio-Control, Inc., of Redmond, Washington, USA.

With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal section 48. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or guiding shaft 44 within body 17. For example, handle 42 may include means to change the length of a guidewire extending through catheter 14 to distal section 48 of shaft 44 or means to steer shaft 44 to place electrode assembly 12 in a preferred location and orientation in the pulmonary vein. Moreover, in some embodiments, handle 42 may be configured to vary the shape, size, and/or orientation of a portion of the catheter. For example, where distal section 48 includes a balloon or basket catheter, handle 42 may be configured to transition distal section 48 from a collapsed state to an expanded state. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14.

Shaft 44 is an elongated, tubular, flexible member configured for movement within body 17. Shaft 44 is configured to support electrode assembly 12 as well as contain associated conductors, and possibly additional electronics used for selecting electrodes to be energized, signal processing, or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

Shaft 44 houses electrode wires (not shown) for carrying electrical current to the electrodes and conducting electrogram signals received by the electrodes. Electrode wires extend between handle 42 and the electrodes within an interior portion of shaft 44. To this end, shaft 44 may include an insulator or insulating material. For example, shaft 44 may be packed with an insulation material and/or a cylindrical layer of insulation material may be circumferentially disposed within an interior portion of shaft 44. The thickness and material characteristics of such insulation are selected to configure shaft 44 for safe use with voltage and current in the range of one thousand volts and/or ten amperes.

In some embodiments, catheter 14 is a hoop catheter, sometimes referred to as a spiral catheter, where electrode assembly 12 includes catheter electrodes (not shown) distributed about a structure of one or more hoops at distal section 48 of shaft 44. The diameter of the hoop(s) may vary. In some embodiments, the hoop catheter has a maximum diameter of about twenty-seven millimeters (mm). In some embodiments, the hoop diameter is variable between about fifteen mm and about twenty eight mm. Alternatively, the catheter may be a fixed diameter hoop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length for electroporation.

In an alternative embodiment, catheter 14 is a basket catheter, where electrode assembly 12 includes catheter electrodes (not shown) distributed about multiple splines at distal section 48 of shaft 44. The number, diameter, and eccentricity of the splines may vary. In some embodiments, the basket catheter includes eight splines. In other embodiments, the basket catheter includes between twelve and sixteen splines. As the number of splines increases, the angular spacing between each catheter electrode is reduced. However, an increased number of splines, and therefore electrodes, require additional wires to sufficiently connect electrode assembly 12 to handle 42 and interface 40. In some embodiments, with an increased number of splines, the number of electrodes per spline is reduced and more concentrated about the equator or within a band centered about the equator and extending, for example, plus or minus 45 degrees in latitude. In yet another alternative embodiment, catheter 14 is a balloon catheter, where electrode assembly 12 includes catheter electrodes (not shown) distributed about a balloon at distal section 48 of shaft 44.

Localization and navigation system 30 may include a visualization system for visualization, mapping, and navigation of internal body structures. System 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, one or more coils (i.e., wire windings) configured to detect one or more characteristics of a magnetic field, for example in the case of a magnetic-field based localization system, or a combination of impedance-based and magnetic-field based localizations systems, such as, for example, the EnSite Precision™ system from St. Jude Medical, Inc.

Localization and navigation system 30 determines respective positions of catheter electrodes relative to the pulmonary vein within which catheter 14 is positioned. The visualization system of localization and navigations system 30 renders and displays the respective positions of catheter 14 and the catheter electrodes in two or three dimensions on display 34b. In certain embodiments, localization and navigation system 30 enables a clinician or physician to visualize the locations of the catheter electrodes relative to the pulmonary vein on display 34b and to select a subset of the catheter electrodes using a user interface, such as, for example, input/output mechanisms 34a. Localization and navigation system 30 enables the clinician or physician to select a subset of electrodes to be energized based on a determination of which electrodes on catheter 14 form a most-concentric ring of electrodes with respect to the central axis of the pulmonary vein. In certain embodiments, localization and navigation system 30 may propose a default subset of electrodes on catheter 14 in lieu of a selection by the clinician or physician.

In alternative embodiments, localization and navigation system 30 automatically determines which catheter electrodes should be energized to achieve a ring of electrodes that is concentric with the central axis of the pulmonary vein. Such an automatic determination may be carried out based on, for example, the determined respective positions of the catheter electrodes, or respective contact of each electrode with the pulmonary vein. For example, in one embodiment, localization and navigation system 30 determines which electrodes form an approximately circular or ellipsoid closed path. In some embodiments, the path is approximately orthogonal to the ostium or antrum of the pulmonary vein being ablated, i.e., the electrodes would lie on a plane that is approximately orthogonal to the central axis of the pulmonary vein. Such a selection may improve the success rate of the ablation procedure. The circular or ellipsoid closed path is found by approximating the catheter as an ellipsoid, a plane is identified that is approximately orthogonal to the pulmonary vein, and an intersection of the plane and ellipsoid is computed according to, for example, P. Klein, *On the Ellipsoid and Plane Intersection Equation*, Applied Mathematics, Vol. 3 No. 11, 2012, pp. 1634-1640.

The ellipsoid that models a basket, balloon, or helical catheter is expressed as, for example:

$$\frac{x^2}{a^2} + \frac{y^2}{b^2} + \frac{z^2}{c^2} = 1 \quad \text{EQ. 1}$$

where, a, b, and c represent the major axes of the ellipsoid.

The plane that intersects the ellipsoid is expressed as, for example:

$$n \cdot (x - x_0) = 0 \quad \text{EQ. 2}$$

where n is the normal vector of the plane and represents the central axis of the pulmonary vein, and $x_0$ is an intersection point through which the plane passes. In an alternative embodiment, the orientation of the plane is user-controlled and may be selected such that the plane is oriented with normal vector, n, misaligned from the central axis of the pulmonary vein. In such an embodiment, a graphical user interface may be provided that enables rotation of the plane with respect to the ellipsoid that represents the catheter, thus enabling the user to select the shape and orientation of the lesion.

Figure 7:
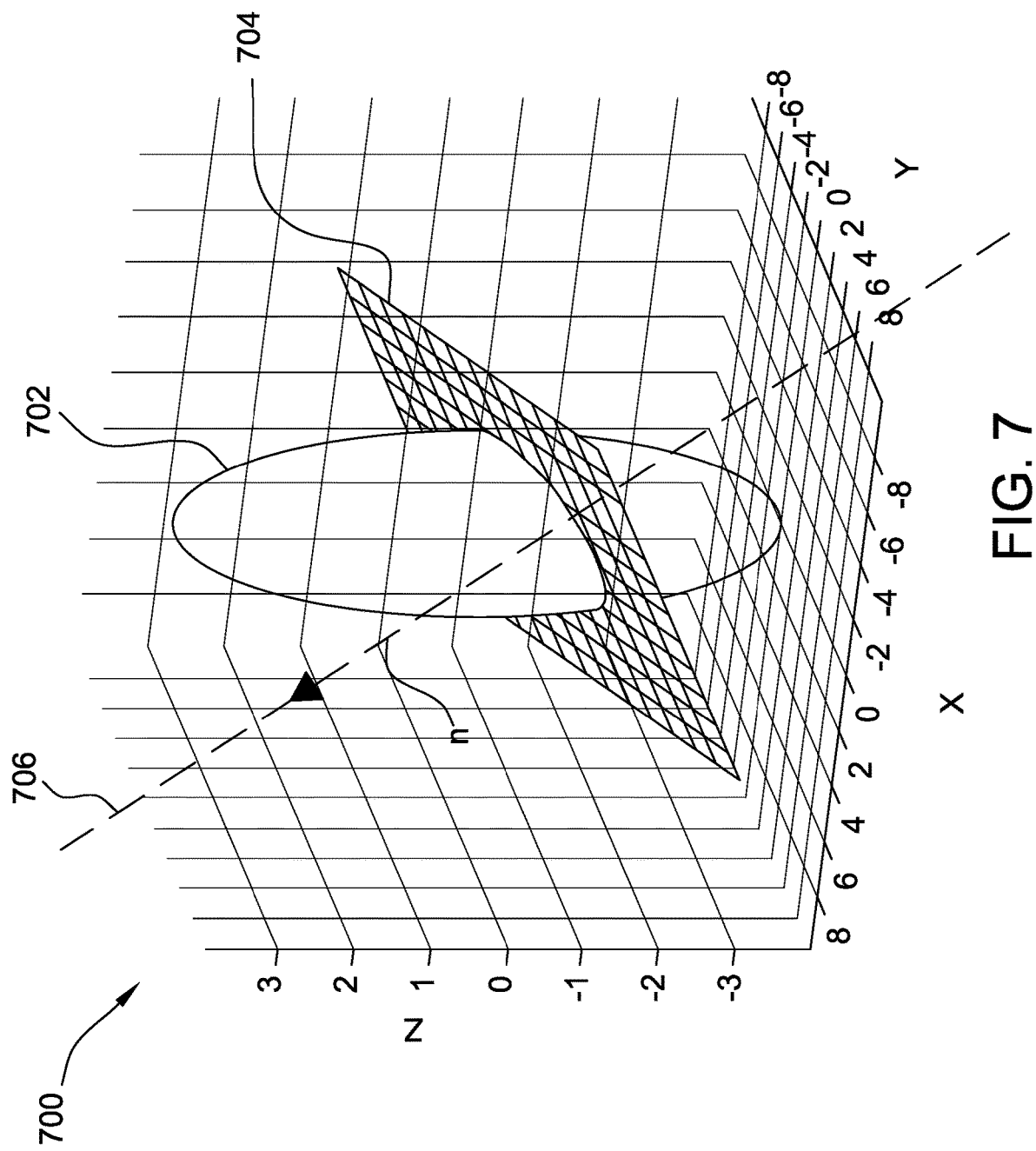
FIG. 7 is a plot illustrating an exemplary intersection of a plane representing a pulmonary vein and an ellipsoid representing a catheter.

The intersection of a plane and an ellipsoid is illustrated in FIG. 7, which shows a plot 700 of an ellipsoid 702 and an intersecting plane 704. The intersection point, $x_0$, defines the depth of the lesion, which can be set more distally or more proximally along the central axis 706 of the pulmonary vein. Given a value for $x_0$, the plane is expressed as:

$$dx+ey+fz+g=0 \qquad \text{EQ. 3}$$

Referring to FIG. 7, the axes of ellipsoid 702 define a coordinate frame. The plane defined in EQ. 3 is then rotated into the coordinate frame defined by the axes of ellipsoid 702.

Generally, the intersection of a plane and an ellipsoid is an ellipse. Such an ellipse generally does not pass exactly through locations of electrodes on the catheter. The catheter electrodes approximate the ellipse to form the closed path. In one embodiment, electrodes within a threshold distance of the plane are selected. In some embodiments, the threshold distance may be defined, for example, as 4.0 mm. In an alternative embodiment, electrodes are selected that are closest to the ellipse that defines the intersection. In such an embodiment, the electrodes are identified by an iterative search, such as, for example, using the gradient decent method. Accordingly, the value of the search distance defines the width of the elliptical path and therefore the lesion. For example, a search distance of 10 mm would yield a wider lesion than a search distance of 4.0 mm.

In certain embodiments, localization and navigation system 30 may include a contact sensing system such as, for example, an electrical impedance sensing system that determines whether a given electrode is in contact with the pulmonary vein. In such embodiments, localization and navigation system 30 considers whether a given electrode is in contact with the pulmonary vein in selecting the subset of catheter electrodes. Electrode-tissue contact may be determined using various technologies, including, for example, imaging, electrogram amplitude, impedance measuring, contact force sensing, ultrasound based distance measurement (e.g., m-mode), and temperature based contact sensing. Temperature based contact sensing operates on the principal that, when an RF current is supplied through the electrodes, electrodes in the blood are cooled and maintain a relatively stable temperature, while electrodes contacting the endocardium typically rise in temperature.

Figure 2:
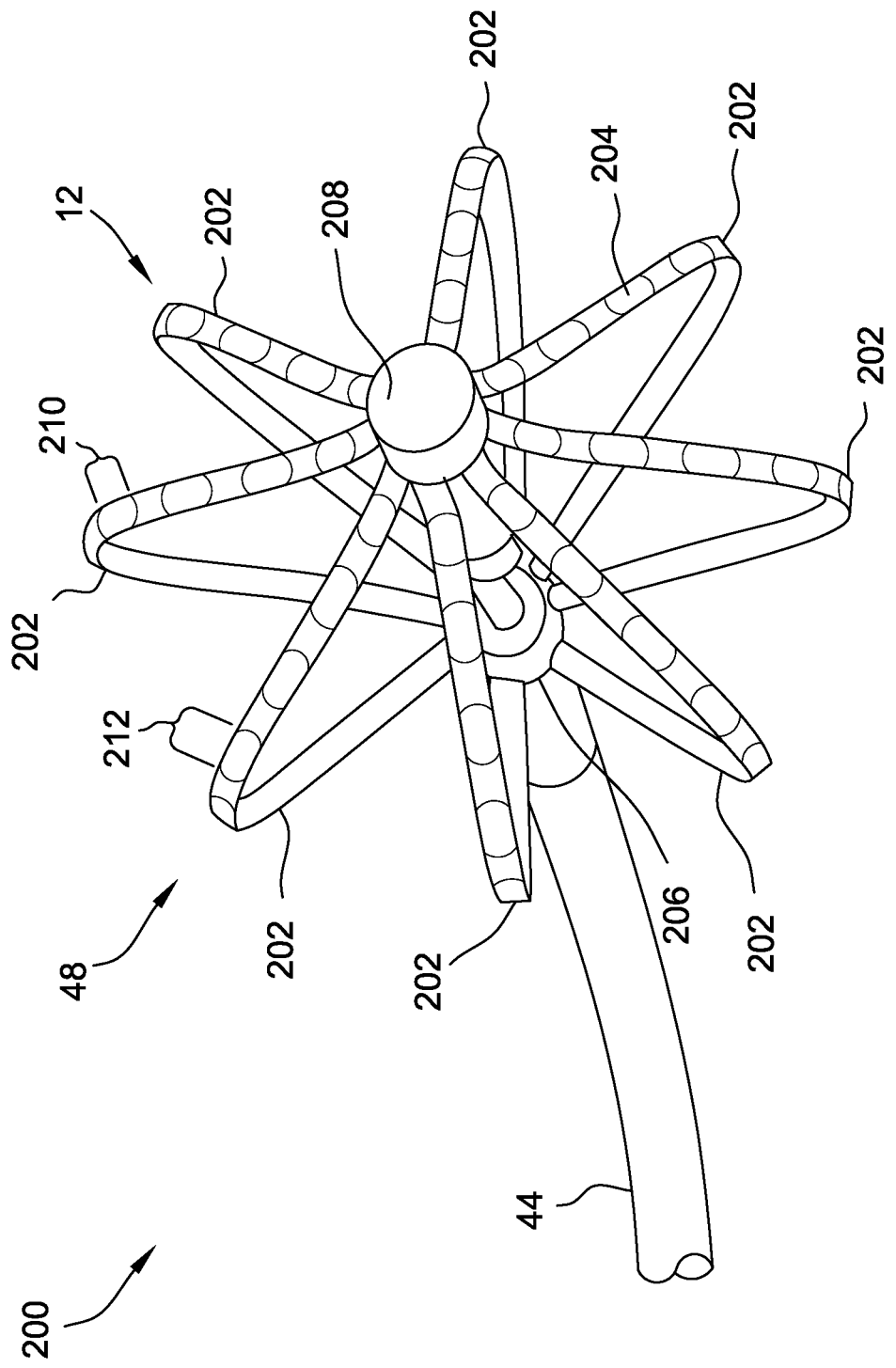
FIG. 2 is a schematic diagram of an exemplary basket catheter for use in the electroporation system shown in FIG. 1.

FIG. 2 is a schematic diagram of an exemplary basket catheter 200 for use in electroporation system 10, shown in FIG. 1. Basket catheter 200 includes shaft 44 illustrated at distal section 48 and, more specifically, at the distal end, to which electrode assembly 12 is coupled. Electrode assembly 12 includes a structure composed of a plurality of splines 202. Each spline 202 of the plurality includes multiple electrodes 204 configured to be individually and selectively energized. Splines 202 define a first pole 206 and a second pole 208 at which splines 202 are joined.

Electrodes 204 are configured for use as electroporation electrodes. In some embodiments, electrodes 204 may be configured for additional uses. For example, one or more of electrodes 204 may perform a location or position sensing function. More particularly, one or more of electrodes 204 may be configured to be a positioning sensor(s) that provides information relating to the location (position and orientation) of catheter 14, and distal section 48 of shaft 44 thereof, in particular, at certain points in time. Accordingly, as catheter 14 is moved along a surface of a structure of interest of tissue 16 and/or about the interior of the structure, the sensor(s) can be used to collect location data points that correspond to the surface of, and/or other locations within, the structure of interest. These location data points can then be used by, for example, a model construction system, in the construction of a three-dimensional model of the structure of interest. In other embodiments, separate catheter electrodes are used for electroporation and positioning.

Electrodes 204 may be evenly distributed about splines 202. Electrodes 204, in the embodiment of FIG. 2, include flexible circuits respectively coupled to the electrodes and powered by conductors housed within shaft 44. Electrodes 204, in alternative embodiments, are platinum ring electrodes configured to conduct and/or discharge electrical current in the range of one thousand volts and/or ten amperes. In certain embodiments, splines 202 of basket catheter 200 are helical splines that rotate about a central axis of electrode assembly 12. Such a helical configuration distributes electrodes 204 more uniformly over the surface of basket catheter 200. In other embodiments, basket catheter 200 may include any suitable number of electrodes 204 made of any suitable material. Electrodes 204 may comprise any catheter electrode suitable to conduct high voltage and/or high current (e.g., in the range of one thousand volts and/or ten amperes). Each catheter electrode 204 is separated from each other catheter electrode by an insulated gap 210. In the example embodiment, each electrode 204 has a same length 212 and each insulated gap 210 has a same length as each other gap 210. In other embodiments, lengths of electrodes 204 and insulated gap 210 may be different from each other. Moreover, in some embodiments, electrodes 204 may not all have the same length 212 and/or insulated gaps 210 may not all have the same length. In some embodiments, electrodes 204 are not evenly distributed about splines 202.

Figure 3:
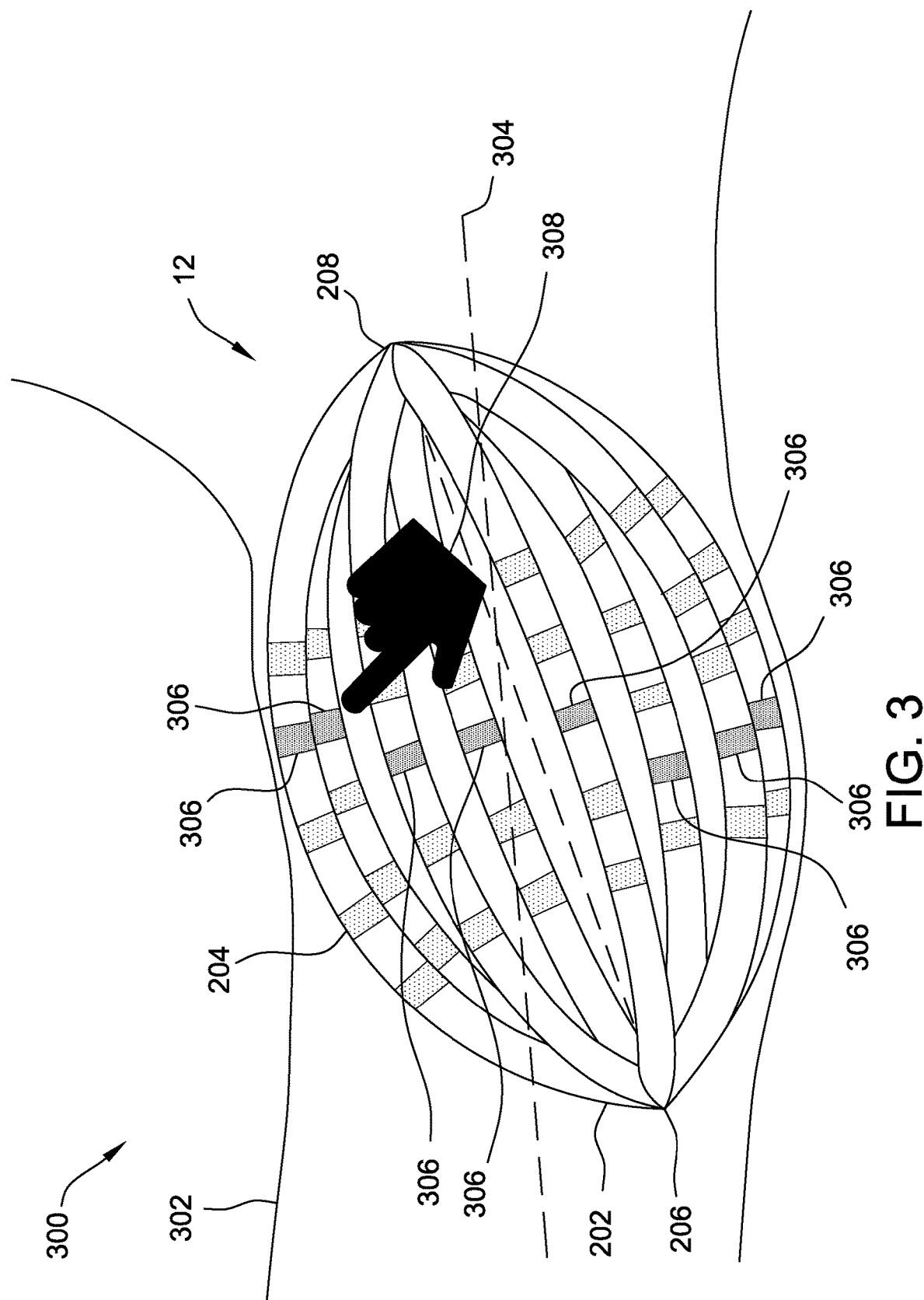
FIG. 3 is a schematic diagram of an exemplary visualization of the basket catheter shown in FIG. 2.

FIG. 3 is a schematic diagram of an exemplary visualization 300 of an exemplary electrode assembly 12 for use in basket catheter 200, shown in FIG. 2. Electrode assembly 12 is positioned in a pulmonary vein 302. Pulmonary vein 302 defines a central axis 304. Electrode assembly 12 includes a plurality of electrodes 204 distributed about splines 202. Splines 202 define first and second poles 206 and 208 where splines 202 join. Electrodes 204 are not evenly distributed about splines 202. Electrodes 204 are concentrated away from first and second poles 206 and 208, because first and second poles 206 and 208 are unlikely to make contact with pulmonary vein 302 when basket catheter 200 is positioned. In other words, electrodes 204 are more likely to contact pulmonary vein 302 when concentrated away from first and second poles 206 and 208.

Visualization 300 illustrates a subset of electrodes 306 that are selected from among electrodes 204. Subset of electrodes 306 may be selected automatically, as described above, or by a user such as a clinician or physician. In certain embodiments, subset of electrodes 306 is initially selected automatically by localization and navigation system 30 based on, for example, each electrode's contact state, and proposed to the clinician or physician operating the system. The system then enables the clinician or physician to confirm or modify the subset of electrodes 306. Subset of electrodes 306 is selected such that electrodes 306 form a path through electrodes 306 that best-approximates a great circle around basket catheter 200 and, further, form a ring of electrodes 306 that is most-concentric with central axis 304 of pulmonary vein 302. Such a ring may, under certain circumstances, be substantially circular or, under certain circumstances, be non-circular. When energized, electrodes 306 form a virtual spiral catheter that delivers DC energy in approximately the same geometric pattern as would be accomplished with an ideally-placed hoop or spiral catheter.

In alternative embodiments, a more-dense array of electrodes 204 is provided on electrode assembly 12 to enable selection of the subset of electrodes 306 that is more concentric with central axis 304 of pulmonary vein 302. Embodiments having fewer electrodes 204 available for selection enable selection of a more approximately concentric ring of electrodes 306.

Visualization 300 further illustrates a user interface 308 for user-selection of the subset of electrodes 306. User interface 308 may be integrated within localization and navigation system 30, shown in FIG. 1, as well as with the visualization system for three-dimensional or two-dimensional display of electrode assembly 12 within pulmonary vein 302.

Figure 4:
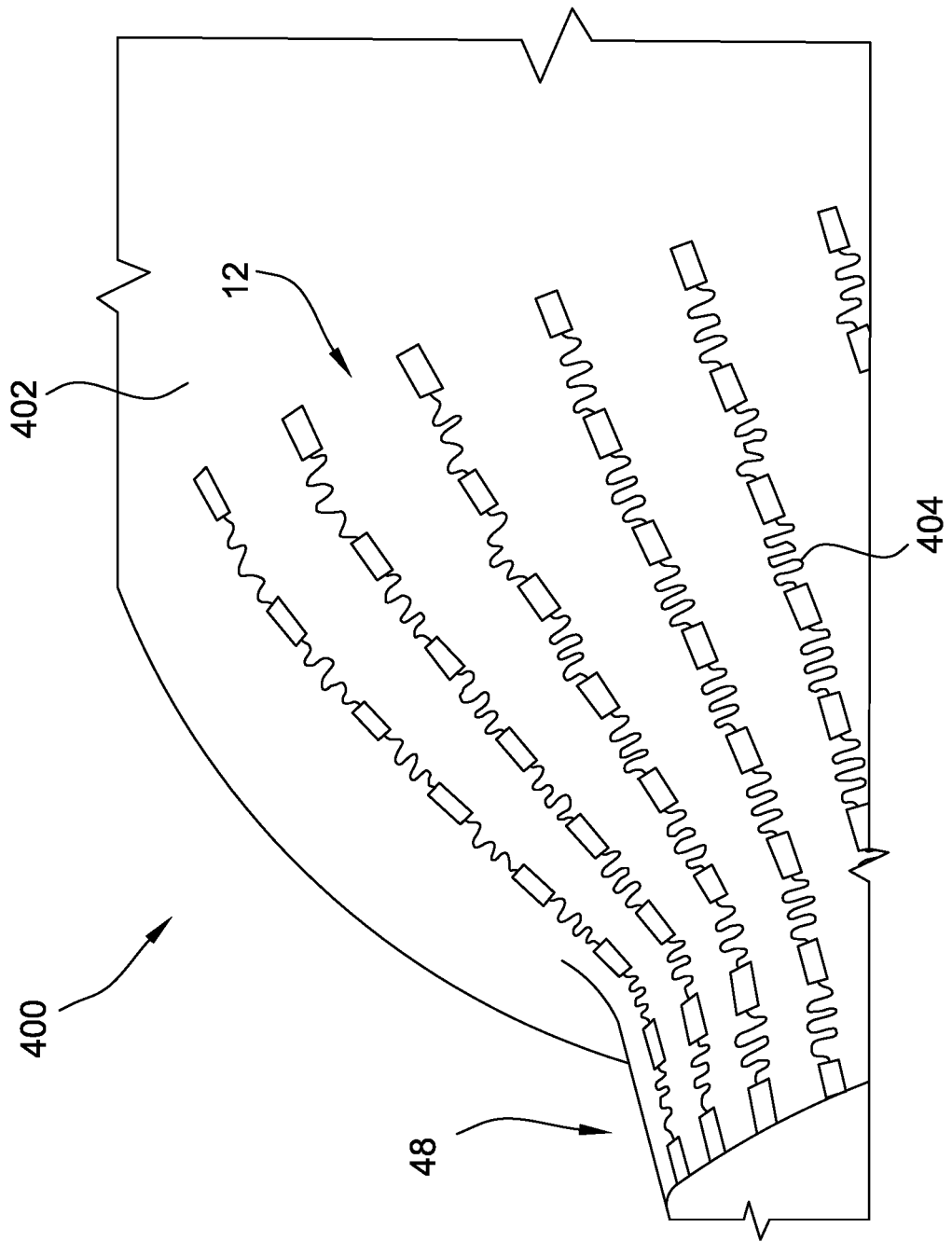
FIG. 4 is a schematic diagram of an exemplary balloon catheter for use in the electroporation system shown in FIG. 1.

FIG. 4 is a schematic diagram of an exemplary balloon catheter 400 for use in electroporation system 10, shown in FIG. 1. Balloon catheter 400 includes a balloon surface 402 expanding from distal section 48 of catheter 14, shown in FIG. 1. Balloon catheter 400 includes electrode assembly 12 having multiple electrodes 404 printed on balloon surface 402. Each of electrodes 404 is configured to be individually and selectively energized to form a ring of electrodes that is concentric with central axis 304 of pulmonary vein 302, both shown in FIG. 3.

Figure 5:
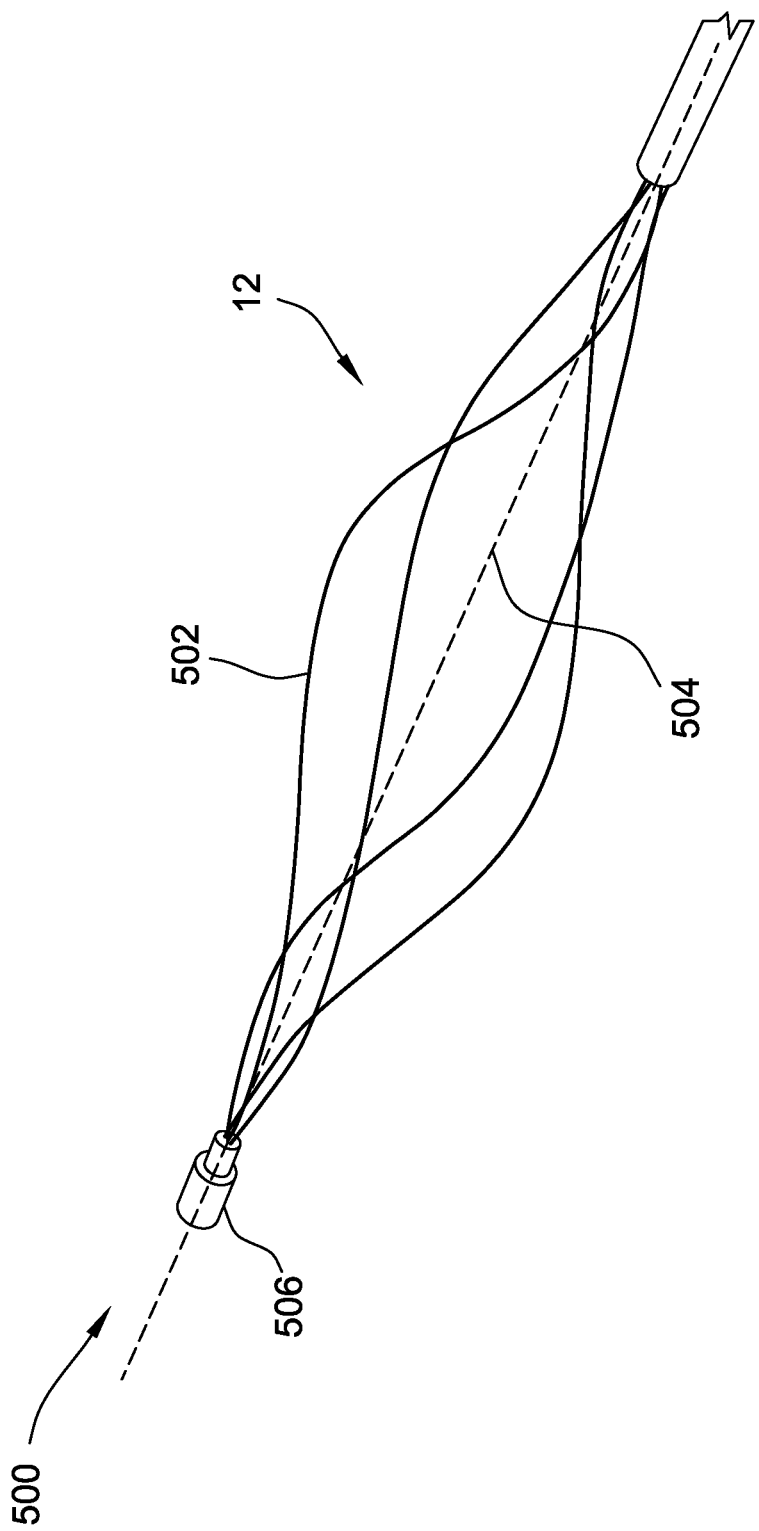
FIG. 5 is a schematic diagram of an exemplary helical catheter for use in the electroporation system shown in FIG. 1.

FIG. 5 is a schematic diagram of an exemplary helical catheter 500 for use in electroporation system 10, shown in FIG. 1. Helical catheter 500 includes a plurality of helical splines 502 that rotate about a central axis 504 and join at an end 506. A plurality of electrodes (not shown) are distributed over helical splines 502 to form electrode assembly 12. Each of the electrodes is configured to be individually and selectively energized to form a ring of electrodes that is concentric with central axis 304 of pulmonary vein 302, both shown in FIG. 3.

Figure 6:
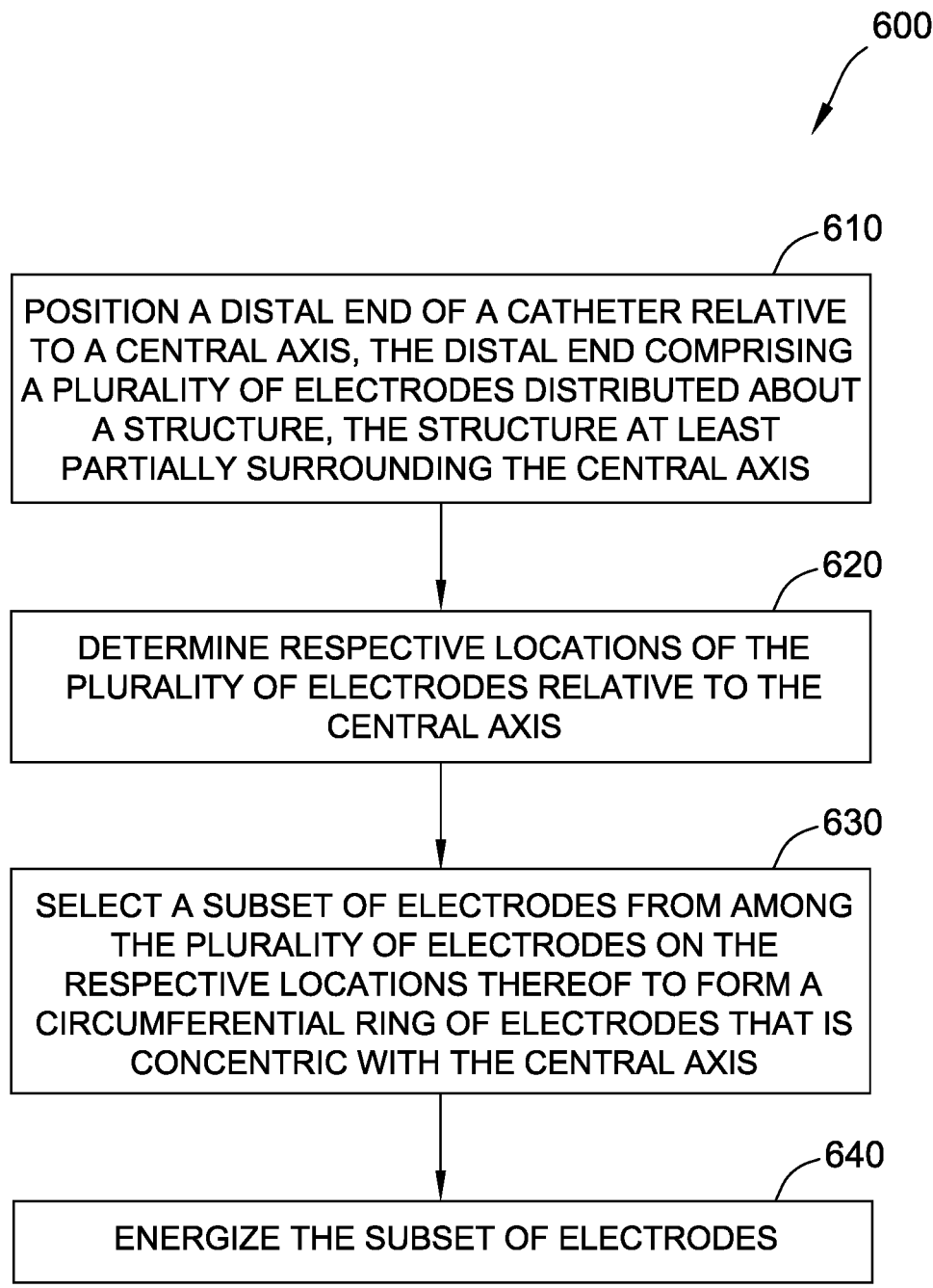
FIG. 6 is a flow diagram of an exemplary method of energizing the catheters shown in FIGS. 1-5.

FIG. 6 is a flow diagram of an exemplary method 600 of energizing catheter 14 and, more specifically, electrode assembly 12, shown in FIGS. 1-4. Referring to FIGS. 1-6, method 600 begins with positioning 610 distal section 48 of catheter 14 relative to a central axis in space, such as, for example, central axis 304 defined by pulmonary vein 302. Distal section 48 is maneuverable to position electrode assembly 12, including electrodes 204, which are distributed about a structure of electrode assembly 12. The structure of electrode assembly 12 may include, for example, splines 202 or balloon surface 402. The structure of electrode assembly 12 at least partially surrounds the central axis.

Once catheter 14 is positioned 610, localization and navigation system 30 determines 620 respective locations of the plurality of electrodes 204 relative to the central axis. A subset of electrodes 306 is then selected 630 based on the respective locations of electrodes 204. Electrodes 306 form a circumferential ring of electrodes that is concentric with the central axis and may be substantially circular or non-circular. Localization and navigation system 30 is configured to select 630 electrodes 306 and to control electroporation generator 26 to energize 640 subset of electrodes 306. Selecting 630 electrodes 306 and energizing 640 electrodes 306 may be carried out by electroporation generator 26 by controlling a network of switches or an addressing circuit that enables the generated DC signal to reach electrodes 306 through shaft 44 to electrode assembly 12 at distal section 48. Accordingly, electroporation generator 26 is further controlled by localization and navigation system 30 to ensure the remaining electrodes of the plurality of electrodes 204 are not energized or, alternatively, the remaining electrodes may be utilized as return electrodes.

The technical effects of the embodiments described above may include: (a) reducing the time necessary to properly position a catheter for delivering electroporation to cardiac tissue; (b) improving concentricity of circumferential lesions with respect to the central axis of targeted veins; (c) improving effectiveness of electroporation therapy; (d) reducing the overall time of electroporation treatment sessions; (e) simplifying positioning of a catheter for delivering electroporation through use of a basket catheter or a balloon catheter in a collapsed state; and (f) improving respective contact of catheter electrodes to cardiac tissue through use of a basket catheter or a balloon catheter.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter comprising:
   a distal section configured to be positioned within a body; and
   an electrode assembly coupled to the distal section, the electrode assembly comprising:
   a plurality of electrodes, each electrode of the plurality of electrodes configured to be selectively energized, wherein a subset of the plurality of electrodes that forms a circumferential ring is configured to be selected by a computing system coupled to the catheter by automatically determining which of the plurality of electrodes form a closed path, wherein the computing system is configured to automatically determine which of the plurality of electrodes form a closed path by:
   approximating the catheter as a geometric shape;

identifying a plane oriented perpendicular to a normal vector;

computing an intersection between the geometric shape and the identified plane; and selecting electrodes of the plurality of electrodes based on the computed intersection.

2. The catheter of claim 1, wherein the electrode assembly further comprises a balloon around which the plurality of electrodes are distributed.

3. The catheter of claim 1, wherein the electrode assembly further comprises a basket having a plurality of splines along which the plurality of electrodes is distributed.

4. The catheter of claim 3, wherein the plurality of splines define first and second poles at which the plurality of splines join, and wherein the plurality of electrodes are concentrated away from the first and second poles.

5. The catheter of claim 1, wherein the circumferential ring of energized electrodes is non-circular.

6. A system comprising:

a catheter comprising an electrode assembly configured to be positioned in a body, the electrode assembly comprising:

a plurality of electrodes, each electrode of the plurality of electrodes configured to be individually energized;

an energy source coupled to the catheter and configured to selectively energize a subset of electrodes of the plurality of electrodes; and a computing system coupled to the catheter and the energy source, the computing system configured to:

detect respective positions of the plurality of electrodes, and select the subset of electrodes to form a circumferential ring of energized electrodes, the computing system configured to select the subset of electrodes by automatically determining which of the plurality of electrodes form a closed path, wherein the computing system is configured to automatically determine which of the plurality of electrodes form a circular or ellipsoid closed path by:

approximating the catheter as a geometric shape;

identifying a plane oriented perpendicular to a normal vector;

computing an intersection between the geometric shape and the identified plane; and selecting, using an iterative search, electrodes of the plurality of electrodes based on the computed intersection.

7. The electroporation system of claim 6, wherein the computing system further comprises a visualization system configured to display the respective positions of the plurality of electrodes.

8. The electroporation system of claim 7, wherein the visualization system is further configured to render a three-dimensional display.

9. The electroporation system of claim 7, wherein the computing system further comprises a user interface configured to enable user selection of the subset of electrodes.

10. The electroporation system of claim 6, wherein the computing system is further configured to detect respective contact of the plurality of electrodes with a vein.

11. A method of energizing a catheter, the method comprising:

positioning a distal section of the catheter within a body, the distal section comprising a plurality of electrodes;

determining respective locations of the plurality of electrodes;

selecting, using a computing device, a subset of electrodes from among the plurality of electrodes by automatically detecting which of the plurality of electrodes form a closed path, wherein the computing device is configured to automatically detect which of the plurality of electrodes form a closed path by:

approximating the catheter as a geometric shape;

identifying a plane oriented perpendicular to a normal vector;

computing an intersection between the geometric shape and the identified plane; and selecting, using an iterative search, electrodes of the plurality of electrodes based on the computed intersection; and energizing the subset of electrodes.

12. The method of claim 11 further comprising displaying the respective positions of the plurality of electrodes on a visualization system.

13. The method of claim 11, wherein the catheter comprises a basket catheter, the method further comprising expanding the basket catheter after positioning the distal section.

14. The method of claim 11, wherein energizing the subset of electrodes comprises:

generating a direct current (DC) signal;

conducting the DC signal through the catheter to the subset of electrodes; and de-energizing remaining electrodes of the plurality of electrodes.

15. The method of claim 11, wherein the catheter comprises a balloon catheter, the method further comprising expanding the balloon catheter after positioning the distal section.

* * * * *